United States Patent [19]

Malatesta et al.

[11] 4,388,242
[45] Jun. 14, 1983

[54] METHOD OF PRODUCTION OF VITAMIN-D

[75] Inventors: Vincenzo Malatesta; Clive Willis; Peter A. Hackett, all of Ottawa, Canada

[73] Assignee: Canadian Patents & Development Limited, Ottawa, Canada

[21] Appl. No.: 358,201

[22] Filed: Mar. 15, 1982

[51] Int. Cl.³ .......................... C07J 17/00; C07J 9/00
[52] U.S. Cl. .................................................. 260/397.2
[58] Field of Search ...................................... 260/397.2

[56] References Cited
U.S. PATENT DOCUMENTS 4,021,423  5/1977  Baggiolini et al. ............... 260/397.2

OTHER PUBLICATIONS

Chem. Abstracts publication vol. 93 (1980), Pars. 46,993Z.

Primary Examiner—Elbert L. Roberts
Attorney, Agent, or Firm—James R. Hughes; Alan A. Thomson

[57] ABSTRACT

A method of upgrading a product containing a minor proportion of pre-vitamin $d_2$ or pre-vitamin $d_3$ and a major proportion of tachysterol comprising irradiating the product with laser light in the wavelength range 330–360 nanometers to obtain a product containing approximately 95% pre-vitamin -$D_2$ or pre-vitamin -$D_3$, and heating this product to convert the pre-vitamin -$D_2$ or pre-vitamin -$D_3$ to vitamin -$D_2$ or vitamin -$D_3$.

2 Claims, 2 Drawing Figures

FIG. I

METHOD OF PRODUCTION OF VITAMIN-D

This invention relates to a method of production of vitamin-D and more particularly to laser photochemical conversion of 7-dehydro-cholesterol to vitamin-$D_3$ and ergosterol to vitamin-$D_2$.

Vitamin D is not a single substance, but only 2 of the 10 or 11 sterols known to have antirachitic properties are of importance medically. These are activated ergosterol and 7-dehydrocholesterol. The D substances are activated sterols complex substances often closely associated with fats in plants and animals. Cholesterol is an important sterol which is present in the skin; activation of cholesterol by ultraviolet light changes the compound and produces vitamin D.

The complex photochemistry of 7-dehydro-cholesterol (7-DHC) and ergosterol (E) is now moderately well understood due to the studies of E. Havinga and his co-workers. See especially the following papers: Loevoet A. L.; Verloop A.; and Havinga E., Red. Trav. Chim., Pays-Bas, 1955, 74,788 and Boosma F.; Jacobs H. J. C.; and Havinga E.; Vancles Gen. A., Tetrahedron Lett. 1975, 7,427.

The present commercial method of vitamin-D production involves a number of fractional crystallizations to isolate the required product. This method is described in French Pat. No: 1,378,122, issued 1964 to K. R. Bhaurichter and F. M. Martin.

The use of photolysis with lasers or other light sources to achieve product separation is now well known. The use of photolysis in the production of vitamin-D is known but present methods have had the problem of the production of side products such as tachysterol, lumisterol and other isomers. These methods have required additional process steps such as fractional recrystalizations to obtain the required separation percentages.

It is an object of the present invention to provide a method of producing vitamin-D that gives improved yields and reduced side product contamination.

This and other objects of the invention are achieved by a method involving photolysis at a selected wavelength.

In drawings which illustrate an embodiment of the invention:

Figure 1:
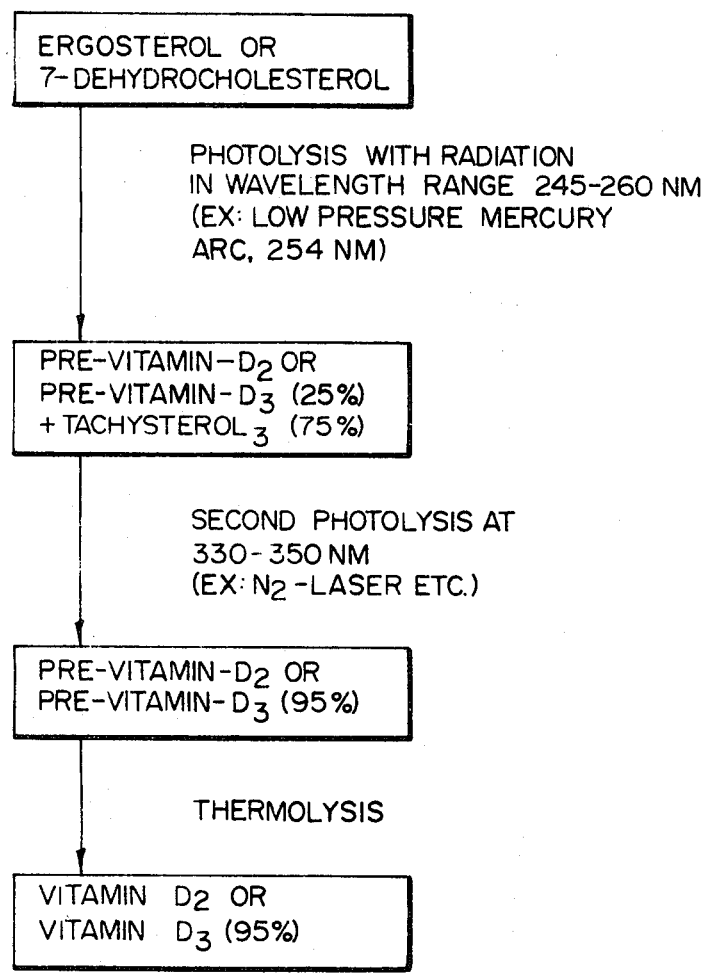
FIG. 1 is a flow diagram of the process.

Referring to FIG. 1, the starting material, 7-dehydro-cholesterol (7-DHC) or ergosterol is irradiated with light in the wavelength range 245–260 nm. A low pressure mercury arc which functions at 254 nm. is most suitable for this. This photolysis may also be achieved by the use of an excimer laser (KrF at 248 nm). Pre-vitamin-$D_3$ or pre-vitamin-$D_2$ (approx. 25%) and tachysterol$_3$ or tachysterol$_2$ (approx. 75%) are formed. This mixture is then irradiated with laser light in the wavelength range 330–360 nm. A nitrogen laser which functions at 337 nm or a YAG laser at 353 nm are suitable for this tep. Other types of lasers may also be used are XeF lasers at 350 nm, Raman shifted XeCl lasers, and broadband dye lasers pumped by XeCl or KrF excimer lasers, the last two being tunable to operate as required in the 330–360 nm range. Continuous, incoherent light sources of proper wavelength may also be used for this step. This second photolysis step produces a mixture that is approx. 95% pre-vitamin-$D_3$ or pre-vitamin-$D_2$. The remaining 5% (approx.) is lumisterol or other isomers. The pre-vitamin-D is then converted to vitamin-D by thermolysis.

Figure 2:
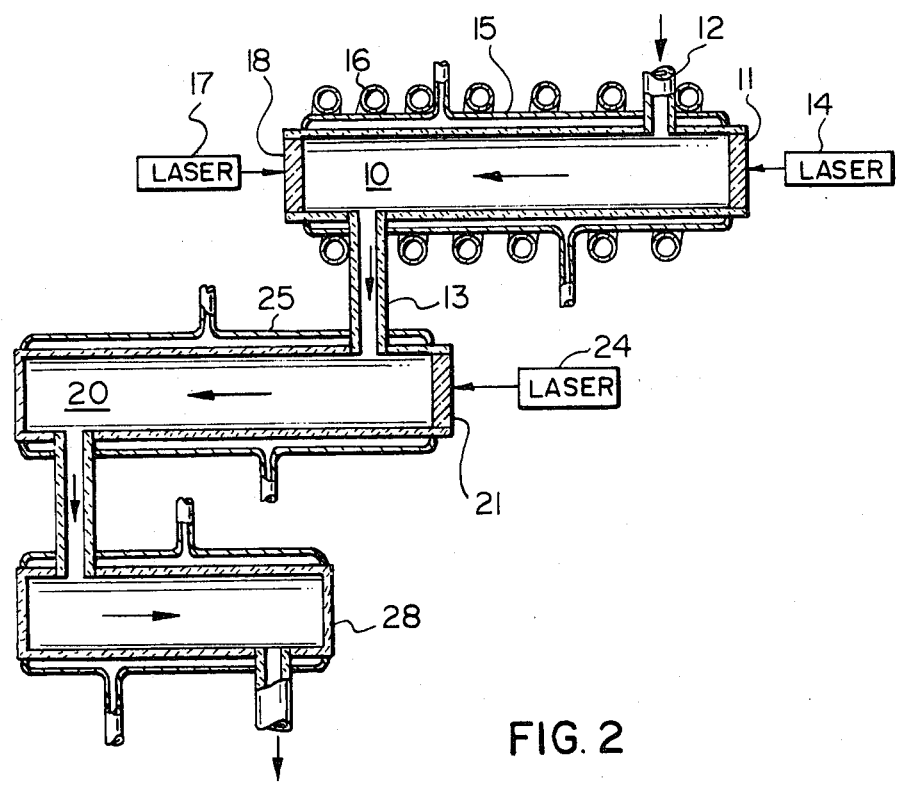
FIG. 2 is a cross-sectional view of apparatus for carrying out the process.

FIG. 2 shows a suitable apparatus arrangement for carrying out the process and includes a reaction chamber 10 preferably of glass having a quartz end window 11 at one end. The starting materials either 7-DHC or ergosterol which are normally solid but which are dissolved in a suitable solvent e.g. di-ethyl ether are fed into port 12 and flow down chamber 10 and out port 13 to the second stage irradiation chamber 20. Light at the selected frequency from laser 14 passes through window 11 and irradiates the material flowing therein. The temperature of the material is held in the range 0°–20° C. by water jacket 15 enveloping chamber 10. This temperature is not critical. The second stage is similar to the first in that the material flowing through chamber 20 is irradiated by a laser beam in the appropriate frequency range from laser 24 passes through quartz window 21 into the flowing mixture. A water jacket 25 maintains the flowing material in the required temperature range. Products from the second stage pass to the thermolysis stage which consists of heating the material to about 60° C. to convert the pre-vitamin $d_2$ or -$d_3$ to vitamin-$d_2$ or -$d_3$.

If in stage 1, a mercury arc lamp is used rather than a laser, then this can readily be achieved by lamp tube 16 helically surrounding chamber 10. In addition it might be convenient to carry out both stages of irradiation in a single chamber. This is done by a second laser 17 at the appropriate frequency irradiating the mixture through quartz end window 18.

In the above description of the process the starting materials are 7-dehydro-cholesterol or ergosterol. The di-hydroxy form of these materials may also be used as starting materials and with the same process as outlined above will produce the di-hydroxy version of the vitamin-$D_3$ or vitamin-$D_2$. It is therefore pointed out that wherein the terminology: 7-dehydro-cholesterol; ergosterol; pre-vitamin-$D_2$ or -$D_3$; and vitamin-$D_2$ or -$D_3$ is used in this disclosure and claims that these terms include the di-hydroxy form of these meterials.

The second stage of the two step irradiation process mentioned above may be readily applied to present methods that produce vitamin-D but with large percentages of tachysterol, lumisterol, or other isomers also produced. The photolysis step using light in the 330–360 nm range provides an efficient and economic method of upgrading the product produced by present methods and avoids the need for derivatization and fractional re-crystallization.

We claim:

1. A method of production of vitamin-$D_2$ or vitamin-$D_3$ using ergosterol or 7-dehydro-cholesterol or their dihydroxy derivatives as the starting materials comprising:
   (a) irradiating the starting material with light in the wavelength range 245–260 nanometers to obtain a product containing pre-vitamin-$D_2$ or pre-vitamin-$D_3$ as a minor proportion and tachysterol$_2$ and tachysterol$_3$ as a major proportion
   (b) irradiating this product with light in the wavelength range 330–360 nanometers to obtain a product containing approximately 95% pre-vitamin-$D_2$ or pre-vitamin-$D_3$, and
   (c) heating this product to convert the pre-vitamin-$D_2$ or pre-vitamin-$D_3$ to vitamin $D_2$ or vitamin $D_3$.

2. A method of upgrading a product containing a minor proportion of pre-vitamin $D_2$ or pre-vitamin $D_3$ and a major proportion of tachysterol comprising:

(a) irradiating the product with light in the wavelength range 330–360 nanometers to obtain a product containing approximately 95% pre-vitamin-$D_2$ or pre-vitamin-$D_3$, and (b) heating this product to convert the pre-vitamin-$D_2$ or pre-vitamin-$D_3$ to vitamin-$D_2$ or vitamin-$D_3$.